United States Patent [19]

Diamond et al.

[11] Patent Number: 5,565,337
[45] Date of Patent: Oct. 15, 1996

[54] HYBRIDOMA-PRODUCING NSO MYELOMA CELL LINE

[75] Inventors: Betty A. Diamond; Subhransu Ray, both of Bronx, N.Y.

[73] Assignee: Albert Einstein College of Medicine of Yeshiva University, a Division of Yeshiva University, Bronx, N.Y.

[21] Appl. No.: 294,416

[22] Filed: Aug. 23, 1994

[51] Int. Cl.⁶ .......................... C12P 21/08; C12N 15/02; C12N 5/12; C07K 16/00

[52] U.S. Cl. .................... 435/70.2; 435/69.7; 435/70.21; 435/172.1; 435/172.2; 435/172.3; 435/240.2; 435/240.21; 435/240.27; 435/240.26; 530/388.1; 530/387.3

[58] Field of Search .......................... 435/240.27, 172.2, 435/70.21, 240.26, 240.2, 240.21, 172.1, 172.3, 172.2, 70.21, 69.7; 530/388.1, 387.3

[56] References Cited

PUBLICATIONS

Morrison, S. L., Science, 229:1202–1207, 20 Sep. 1985.
Sinbovics, J. G., Acta Microbiol Hung (Hungary), 38(3–4):321–34, 1991.

*Primary Examiner*—Lila Feisee
*Assistant Examiner*—Susan A. Loring
*Attorney, Agent, or Firm*—Amster, Rothstein & Ebenstein

[57] ABSTRACT

This invention relates to an NSO myeloma cell line which has increased fusion frequency, and to a method of producing said cell line. The NSO cell line of the invention, when fused with B cells, produces monoclonal antibody-secreting hybridoma which has increased resistance to death. In addition, the monoclonal antibodies secreted by said hybridomas have increased affinity for foreign antigens and for autoantigens.

12 Claims, 5 Drawing Sheets

5,565,337

HYBRIDOMA-PRODUCING NSO MYELOMA CELL LINE

This invention was made with U.S. Government support under NIH Grant Nos. R01-AR32371, P01-AI33184 and T32-GM07288. The U.S. Government has certain rights in this invention.

FIELD OF THE INVENTION

This invention relates to an NSO myeloma cell line useful in the production of hybridomas, and to a method of producing said NSO myeloma cell line. The NSO myeloma cell line of the invention has a high fusion frequency, and is therefore more effective in producing hybridomas when fused to B cells. Further, the hybridomas produced utilizing the NSO myeloma cell line of the invention have greater resistance to death. In addition, monoclonal antibodies secreted by said hybridomas have high affinity for foreign antigens and for self antigens.

BACKGROUND OF THE INVENTION

B cells are lymphoid stem cells from the bone marrow that migrate to and become mature antigen-specific cells in the spleen and lymph nodes. Many immature B cells are found in the spleen which, because of the large amount of blood passing through it, provides many chances for the B cells to become exposed to new antigens. This promotes differentiation of the B cells into functional cells. Mature B cells are capable of being stimulated by specific antigens which enter into the body. After B cells come in contact with antigens, they change into plasma cells and produce antibodies which destroy the invading antigens. This antigen-antibody reaction is known as the specific immune response.

Hybridoma cell lines are created by fusing B cells with NSO murine myeloma cells. These myeloma cells are from tumors which originate in the bone marrow. When B cells and NSO myeloma cells are fused, hybridomas are produced, which hybridomas secrete monoclonal antibodies.

Monoclonal antibodies are exceptionally pure and antigen-specific antibodies. Monoclonal antibodies are used to identify antigens on viruses and bacteria, and are also used in tissue and blood typing. Further, monoclonal antibodies can be used to identify hormones, to diagnose infectious diseases and to identify tumor antigens.

When certain populations of B cells are used to produce monoclonal antibodies, low affinity antibodies, which do not bind effectively with antigens, are produced. Further, some B cells undergo apoptotic cell death, especially B cells making antibodies to self-antigens, and do not result in the production of viable hybridomas. Therefore, a need exists to develop hybridomas which are more resistant to death, which hybridomas secrete monoclonal antibodies which are high affinity, and therefore bind effectively to antigens.

Further, when B cells proliferate in lymphoid organs, somatic mutations of immunoglobulin genes occurs, which leads to the generation of clonally related B cells which have diversified antigen receptors. Within this population of B cells, antigen selection results in affinity maturation. As pathogenic autoantibodies are encoded by somatically mutated immunoglobulin genes, autoantigenic specificity may be acquired by the process of somatic hypermutation. These autoreactive cells represent the pathogenic B cells of autoimmune disease.

Autoimmune diseases are diseases which are produced when the body's normal tolerance of its own antigenic markers on cells disappears. Autoantibodies are produced by B cells, and these autoantibodies attack normal cells whose surface contains a "self" antigen or autoantigen. This results in the destruction of tissue. Therefore, a need exists to develop monoclonal antibodies which are specific for, bind to and thereby inactivate cells which produce autoantibodies.

It is therefore an object of this invention to provide a cell line which has a high fusion frequency when used to produce monoclonal antibody-secreting hybridomas.

It is a further object of this invention to provide monoclonal antibody-secreting hybridomas which have increased resistance to death.

It is another object of this invention to provide a method of producing monoclonal antibody-secreting hybridomas which have increased resistance to death.

It is a still further object of this invention to provide hybridomas which secrete monoclonal antibodies which have increased affinity for foreign antigens.

It is a yet another object of this invention to provide monoclonal antibodies which have increased affinity for autoantibody-producing cells.

SUMMARY OF THE INVENTION

This invention is directed to $NSO^{bcl-2}$ myeloma cells and to methods of producing said cells. The $NSO^{bcl-2}$ myeloma cells of the invention have high fusion frequency, and are fused with B cells to produce hybridomas which have increased resistance to death.

The $NSO^{bcl-2}$ myeloma cells of the invention comprise NSO myeloma cells which are transfected with a plasmid containing the bcl-2 gene. Additionally, the plasmid contains an immunoglobulin heavy chain enhancer. The $NSO^{bcl-2}$ myeloma cells of the invention are used to produce monoclonal antibody-secreting hybridomas. The monoclonal antibodies secreted by said hybridomas have increased affinity for foreign antigens and for autoantigens.

This invention is further directed to a method of treating autoimmune disease comprising the administration of monoclonal antibodies secreted by hybridomas produced utilizing the $NSO^{bcl-2}$ myeloma cells of the invention.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 2A shows RNA probed with 850-bp I/Apa Ibcl-2 fragment and FIG. 2B shows ethidium bromide-stained gel prior to transfer onto nitrocellulose;

DETAILED DESCRIPTION OF THE INVENTION

Figure 1:
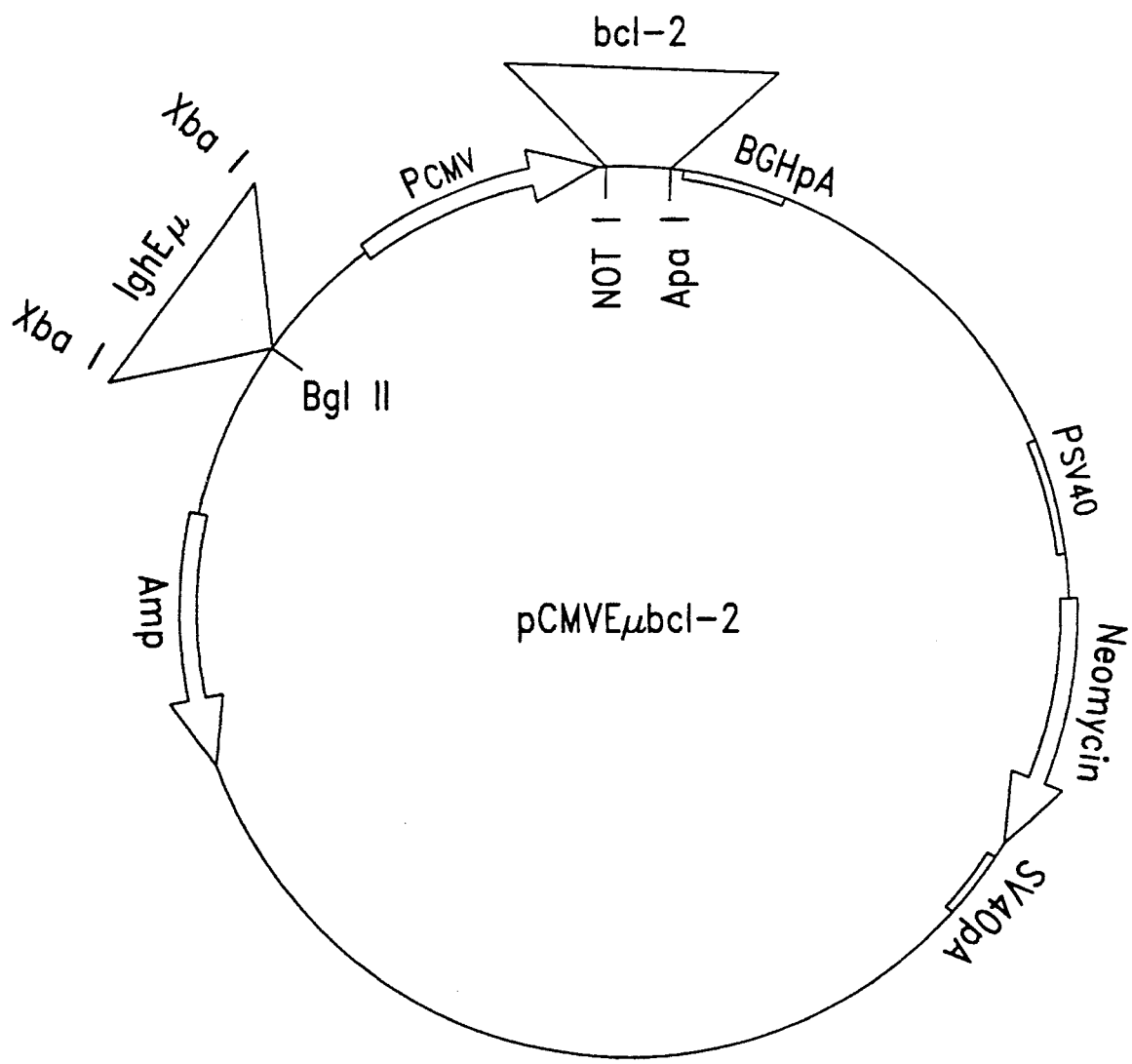
FIG. 1 represents a bcl-2 vector which is regulated by a constitutive cytomegalovirus promoter (Pcmv) under the influence of the immunoglobulin heavy chain enhancer.
Figure 2:
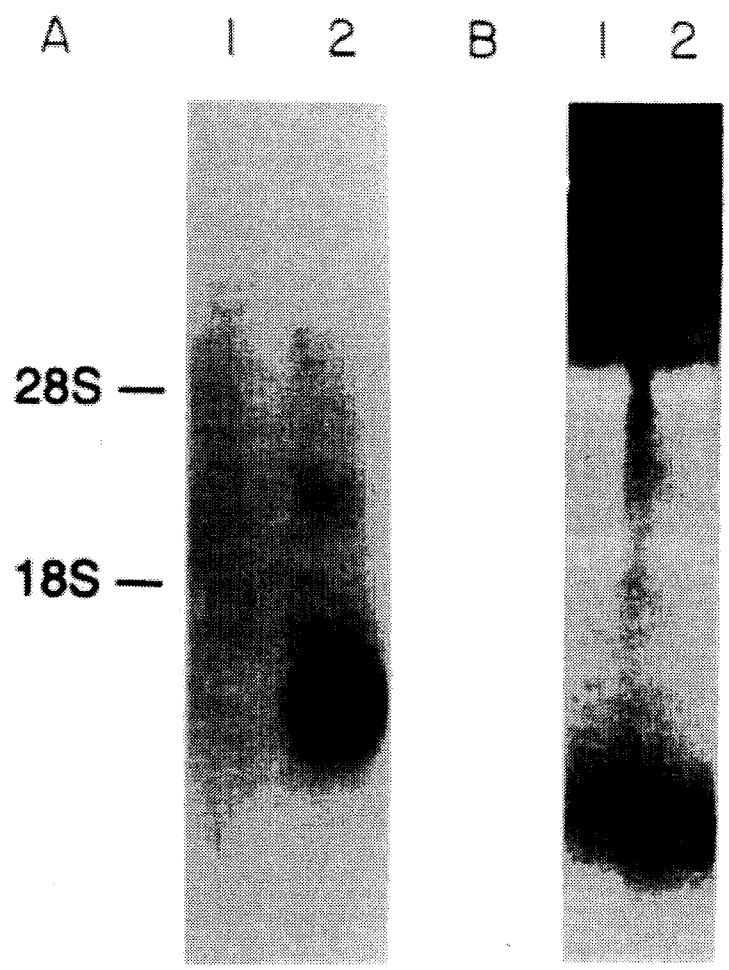
FIGS. 2A and 2B represent the expression of bcl-2 RNA as shown by Northern analysis.

In order to produce the NSO$^{bcl-2}$ cell line of the invention, NSO myeloma cells were transfected with plasmid pcMVEμ.bcl-2, which contained bcl-2 gene and an immunoglobulin heavy chain enhancer. First, plasmid pCMVEμ.bcl-2 was constructed. An 850 bp fragment was isolated from pbluebcl-2 (see Cleary et al., Cell, Vol. 47, pp. 19–28 (1986)) by digestion with NotI and ApaI and inserted into the cloning site of pRC/CMV (Invitrogen Corp.) using standard cloning protocols. A 1kb XbaI fragment encompassing the heavy chain enhancer was inserted into the BglII site (see Hung et al., Nuc. Acids Res., Vol. 12, pp. 1863–1874 (1984)). The construct (see FIG. 1) was then transfected into NSO myeloma cells by electroporation at 600 V, 25 uF, ∞Ω, Tc=1.1 and selection was carried out in 2 mg/ml geneticin. In addition, NSO cells were transfected with pRC/CMV vector alone. Expression of bcl-2 RNA was confirmed by Northern analysis probed with the 850 bp bcl-2 fragment (see FIG. 2).

In order to assay for apoptosis, NSO, NSO$^{pRC/CMV}$, and NSO$^{bcl-2}$ were incubated with 1 μM staurosporine for 18 hours prior to DNA extraction. The cells were pelleted and resuspended in cell lysis buffer (5 mM Tris HCL, pH 7.5/20 mM EDTA/0.5% Triton X-100) for twenty minutes on ice. After centrifugation, the supernatant was treated with RNase A (100 μg/ml) and proteinase K (200 μg/ml). The solution was phenol and phenol/chloroform extracted. The DNA was precipitated in sodium acetate and ethanol and analyzed on a 1% agarose gel.

To perform fusions with primary spleen cells, spleen cell suspensions were prepared at 4° C. The splenocytes were divided into two equal populations and fused with either the NSO or NSO$^{bcl-2}$ myeloma partner according to standard procedures. Wells were scored for hybridoma growth after 10 days. All BALB/c mice used in this study were 6–8 weeks of age. For antigen-activated splenic fusion, BALB/c mice were immunized intraperitoneally with 100 μg of keyhole limpet hemocyanin (KLH) in complete Freund's adjuvant. One month later, the mice were injected intravenously with 25 μg of phosphocholine coupled to KLH (PC-KLH) in 0.9% NaCl solution and 12 days later were injected with 100 μg PC-KLH. Immunized mice were sacrificed on days 2, 5, 7, and 9 following the final immunization. The transgenie mice utilized in this study were 6–8 weeks of age.

Figure 3:
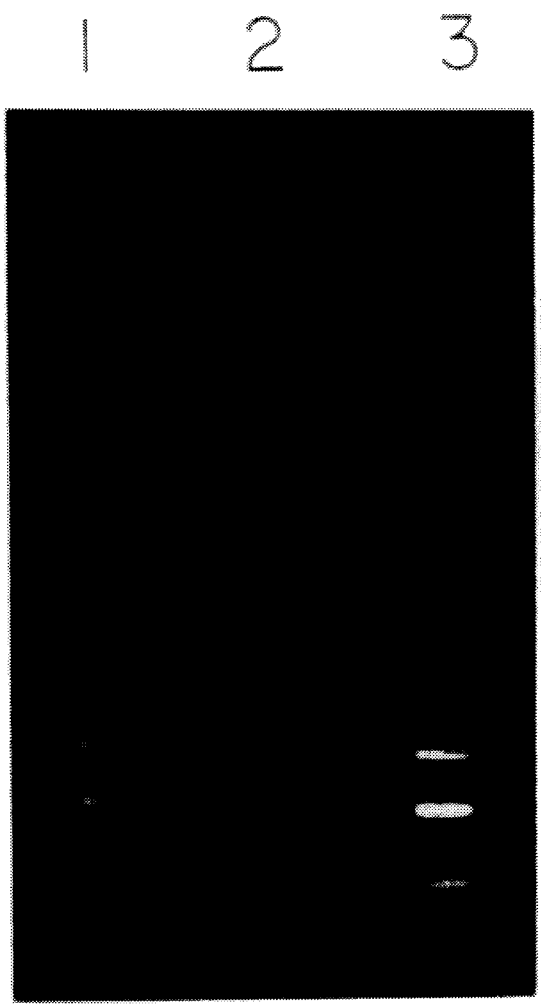
FIG. 3 represents gel electrophoresis of DNA extracted from NSO cells (lane 1), $NSO^{pRC/CMv}$ cells (lane 3) and $NSO^{bcl-2}$ cells (lane 2) following treatment with 1 μM staurosporine.

In order to determine whether bcl-2 expression could rescue NSO$^{bcl-2}$ from signals that mediate apoptosis, NSO, NSO$^{pRC/CMV}$ and NSO$^{bcl-2}$ cells were treated with staurosporine, a protein kinase inhibitor and known inducer of apoptosis. Following treatment with staurosporine, NSO cells displayed the morphological and biochemical changes characteristic of apoptosis. In contrast, the transfected NSO myeloma cells (NSO$^{bcl-2}$) did not undergo staurosporine-induced apoptosis. Instead, NSO$^{bcl-2}$ displayed increased resistance to apoptosis. NSO$^{pRC/CMV}$ behaved like untransfected cells (see FIG. 3).

It was determined that NSO$^{bcl-2}$ fusions show an increased representation of IgG-secreting B cells. Whether the susceptibility of NSO to apoptosis could bias the repertoire of hybridomas obtained from spleen cell fusions was determined. Initial fusions performed with spleen cells from unimmunized BALB/c mice revealed an increased yield of hybridomas with NSO$^{bcl-2}$ as compared to NSO (see Table 1 below). In order to determine whether this simply reflected an overall increase in fusion efficiency or was specific to a particular B-cell population, fusions with spleen cells from immunized mice were performed. Following secondary immunization with PC-KLH, NSO$^{bcl-2}$ demonstrated a 2–5-fold increase in hybridoma production as compared to NSO (see Table 1).

TABLE 1

Hybridoma Yields From Splenic Fusions

| Mouse | Fusion Partner | Wells With Hybridomas No. | % |
|---|---|---|---|
| Naive BALB/c | | | |
| 1 | NSO | 108/480 | 22 |
| | NSO$^{bcl-2}$ | 286/480 | 60 |
| 2 | NSO | 106/480 | 22 |
| | NSO$^{bcl-2}$ | 229/480 | 48 |
| 3 | NSO | 121/864 | 14 |
| | NSO$^{bcl-2}$ | 300/797 | 38 |
| Immunized BALB/c | | | |
| Day 2 | NSO | 39/720 | 5 |
| | NSO$^{bcl-2}$ | 96/346 | 28 |
| Day 5 | NSO | 60/900 | 6 |
| | NSO$^{bcl-2}$ | 117/900 | 13 |
| Day 7 | NSO | 55/1015 | 5 |
| | NSO$^{bcl-2}$ | 159/1015 | 16 |
| Day 9 | NSO | 21/120 | 17 |
| | NSO$^{bcl-2}$ | 55/60 | 92 |
| Transgenic | | | |
| 1 | NSO | 132/480 | 28 |
| | NSO$^{bcl-2}$ | 291/480 | 61 |
| 2 | NSO | 95/960 | 10 |
| | NSO$^{bcl-2}$ | 173/689 | 25 |

Among the hybridomas secreting immunoglobulin, there was a significant increase in the percentage of IgG-producing clones (67% vs. 46%, P less than 0.005) in the NCO$^{bcl-2}$ fusion (see Table 2 below). This increase occurred in the absence of any significant increase in the percentage of hybridomas secreting IgM. This data is consistent with NSO$^{bcl-2}$ leading to a preferential representation of antigen-activated B cells. In three additional fusions performed with primary PC-KLH-immunized BALB/c spleens, a similar difference (P less than 0.005) was observed in the percentage of IgG clones obtained with either NSO$^{bcl-2}$ (213/412, 52%) or NSO (105/328, 32%). Again, there was no appreciable difference in the percentages of IgM-secreting hybridomas (22% vs. 24%, respectively).

TABLE 2

Isotope and Antigenic Specificity of Hybridomas From immunized Mice

| Experiment | Fusion Partner | IgM+ Hybridomas | | | | IgG+ Hybridomas | | | |
|---|---|---|---|---|---|---|---|---|---|
| | | Total | % | PC-KLH Specific | % | Total | % | PC-KLH Specific | % |
| Immunized BALB/c | | | | | | | | | |
| Day 2 | NSO | 3/30 | 10 | 2/3 | 66 | 19/30 | 63 | 16/19 | 84 |
| | NSO$^{bcl-2}$ | 5/72 | 7 | 5/5 | 100 | 62/72 | 86 | 58/62 | 94 |
| Day 5 | NSO | 22/58 | 38 | 10/22 | 45 | 15/58 | 26 | 9/15 | 60 |
| | NSO$^{bcl-2}$ | 18/83 | 22 | 10/18 | 56 | 38/83 | 46 | 20/38 | 53 |
| Day 7 | NSO | 6/38 | 16 | 3/6 | 50 | 24/38 | 63 | 12/24 | 50 |
| | NSO$^{bcl-2}$ | 24/120 | 20 | 11/24 | 46 | 83/120 | 69 | 53/83 | 64 |
| Total | NSO | 31/126 | 25 | 15/31 | 48 | 58/126 | 46 | 37/58 | 64 |
| | NSO$^{bcl-2}$ | 47/275 | 17 | 26/47 | 55 | 183/275 | 67 | 131/183 | 72 |

It was then determined whether resistance of NSO$^{bcl-2}$ to apoptosis may lead to a more complete representation of the peripheral B-cell repertoire, specifically leading to a more accurate evaluation of the extent of autoreactivity present in the periphery of non-autoiummune mice. Fusions with spleen cells from transgenic mice in which a large percentage of peripheral B cells express the transgenic IgG2b heavy chain of an anti-double-stranded DNA (dsDNA) antibody were performed. It was demonstrated that although these mice have low serum titers of IgG2b and express no anti-dsDNA activity in their serum, they harbor in their spleen a population of anergic cells expressing transgene encoded anti-dsDNA antibody. Furthermore, there is a population of splenic B cells in these mice that undergoes apoptosis in vivo that is not seen in nontransgenic littermates.

Many fusions of unstimulated splenic cells from these mice with NSO failed to yield hybridomas producing transgene encoded anti-dsDNA antibodies. To sample this autoreactive B-cell repertoire, spleen cells from transgenic mice were fused to NSO$^{bcl-2}$ cells. A greater yield of hybridomas with NSO$^{bcl-2}$ cells was obtained (Table 1). In addition, a greater percentage of the surviving hybridomas in the NSO$^{bcl-2}$ fusion were secreting IgG2b encoded by the transgene than in the fusion with NSO cells (Table 3). While none of 103 IgG2b-secreting hybridomas generated with NSO produced an anti-dsDNA antibody, 16 of 248 IgG2b-expressing lines (6.5%) generated with NSO$^{bcl-2}$ were DNA binding. Thus, the NSO$^{bcl-2}$ fusion partners displayed the unique ability to form hybridomas with autoreactive B cells and enabled transformation of a population of anergic autoreactive B cells that are programmed for apoptosis.

TABLE 3

Fusions with IgG2b transgenic mice

| Experiment | Fusion Partner | Hybridomas secreting IgG2b No. | % |
|---|---|---|---|
| 1 | NSO | 23/94 | 25 |
| | NSO$^{bcl-2}$ | 109/186 | 59 |
| 2 | NSO | 10/70 | 14 |
| | NSO$^{bcl-2}$ | 25/86 | 29 |

Figure 4:
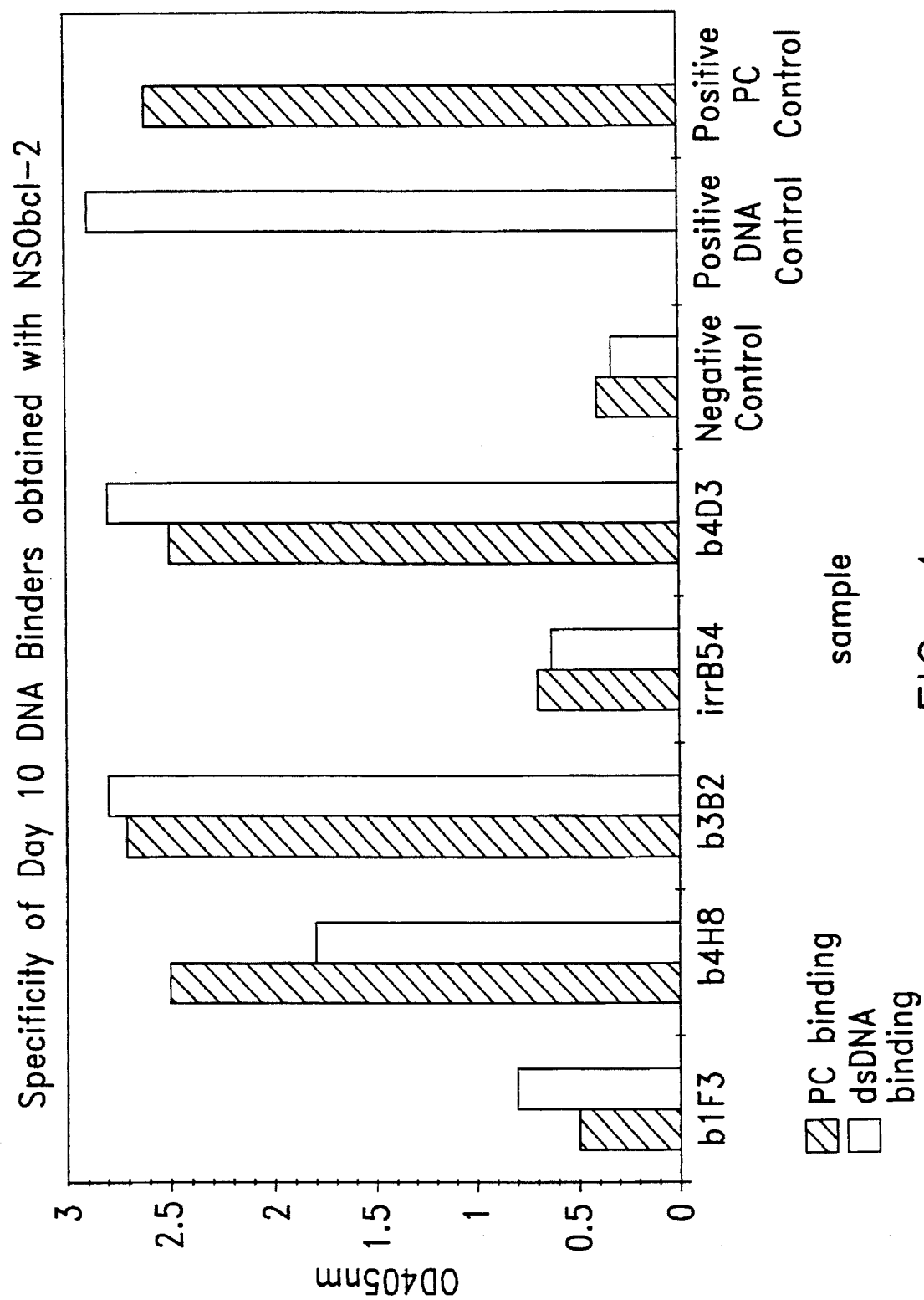
FIG. 4 represents the ability of NSO and NSO$^{bcl-2}$ cells to immortalize splenic B cells from phosphocholine-carrier (PC-KLH) immunized mice.

NSO$^{bcl}$-2 immortalized a population of splenic B cells from phosphocholine-carrier (PC-KLH) immunized mice that demonstrates reactivity to both the eliciting antigen, PC, as well as to a self epitope, double stranded DNA (see FIG. 4). The NSO fusion partner was not able to generate viable hybridomas with the same B cell population. NSO$^{bcl-2}$ allows for evaluation of the in mechanisms that play a role generating autospecificities, such as somatic hypermutation, as well as the factors that regulate potentially deleterious antibodies in vivo.

Figure 5:
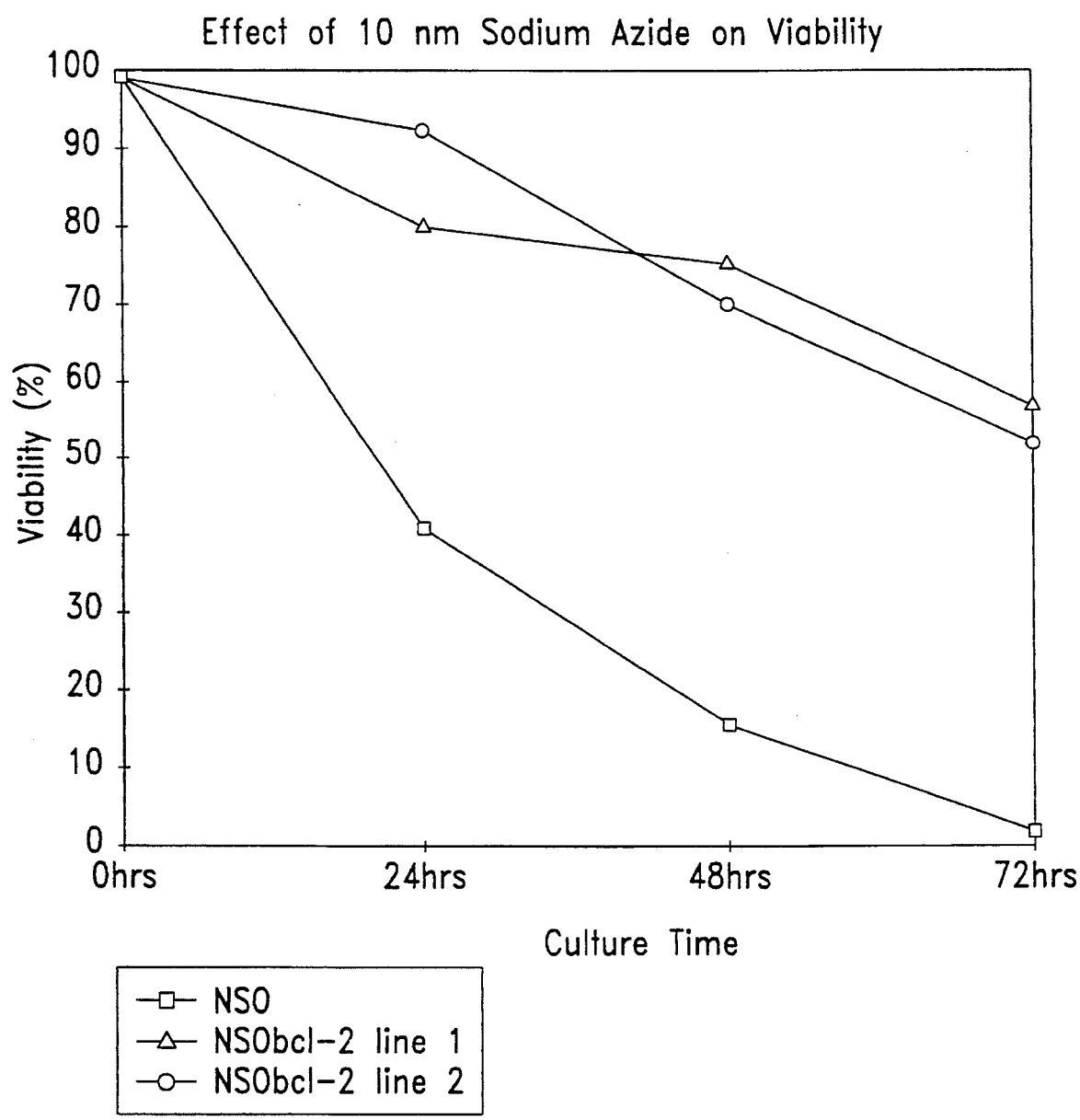
FIG. 5 represents the ability of NSO$^{bcl-2}$ cells to resist sodium azide, a chemical substance which inhibits metabolic respiration.

Further, NSO$^{bcl-2}$ cells showed increased resistance to sodium azide, a chemical substance which inhibits metabolic respiration and therefore is toxic to many living organisms including various bacteria (See FIG. 5). At sodium azide concentrations which are toxic to bacterial survival, the NSO$^{bcl-2}$ showed greater than 60% viability even after three days in culture. It was also shown that NSO$^{bcl-2}$ cells, upon being removed from the sodium azide, were able to fully recover both viability and proliferative capacities. Since culture contamination is a common problem in in vitro cell maintenance, a cell line that displays increased resistance to anti-microbial drugs provides a tremendous advantage in tissue culture techniques.

Hybridomas derived from the NSO$^{bcl-2}$ fusion partner cells displayed features resulting from bcl-2 expression that facilitated the analysis of such clones. It was found that the increased resistance to apoptosis allows hybridomas to survive longer despite nutrient depletion, to grow to higher density, and to achieve a higher cloning efficiency. The results from transfection of bcl-2 into the NSO fusion partner cells indicates that the genes for other molecules (growth factors, accessory molecules, or growth factor receptors) can be transfected into NSO fusion partner cells to isolate previously inaccessible B cells, including those in various stages of B cell development.

Plasmids containing genes which confer increased resistance to apoptosis or other cell death mechanisms can be transfected into fusion partners, including ced-9, bax, bcl-$X_L$, bcl-$X_s$, ICE, P53 and myc. Further, plasmid constructs containing genes which encode growth or survival factors, such as cytokines, or anti-sense mRNA that blocks expression of particular apoptosis inducing proteins can be utilized for transfection into fusion partners. B cells, including SP2 and NS1, as well as T cells, including BW5147, can be used as fusion partners. Constitutive promoters, including CMV promoter, inducible promoters and cell-specific promoters can be utilized.

Anti-dsDNA antibodies obtained from mice and humans with the autoimmune disease systemic lupus erythematosus are somatically mutated, suggesting that autoreactive B cells may routinely arise among lymphoid organ germinal center B cells activated by foreign antigens. This demonstrates that autoreactive splenic B cells reside in peripheral lymphoid organs in a state that is inaccessible by fusion with non-transfected NSO cells. Fusion with NSO$^{bcl-2}$ cells captures these cells and permits a study of the generation and regulation of these autoreactive B cells arising in non-autoimmune as well as autoimmune mice.

The bcl-2 transfected NSO myeloma cells of the invention (NSO$^{bcl-2}$) were deposited with the American Type Culture Collection, Rockville, Md., on Aug. 16, 1994 and catalogued as ATCC No. CRL 11705. These cells demonstrated an increased fusion frequency when fused with primary B cells from the spleen. Further, hybridomas generated utilizing the NSO$^{bcl-2}$ myeloma cells of the invention are much more resistant to death, showing increased stability in response to stressful conditions such as high cell density, freezing and thawing, and medium depletion. The monoclonal antibodies secreted by these hybridomas show a greater representation of specificities for self-antigens as well as possessing characteristics of affinity-matured antibodies.

The NSO$^{bcl-2}$ myeloma cells of the invention can be used in the production of high affinity antibody-secreting hybridomas. The cell line is much easier to grow, requires less feeding and less attention to cell density, and will facilitate the production of antibodies to foreign antigens and to self antigens, and can therefore be administered to treat autoimmune disease, including systemic lupus erythematosus, diabetes mellitus, rheumatoid arthritis, ulcerative colitis, myasthenia gravis and multiple sclerosis.

Although the invention herein has been described with reference to particular embodiments, it is to be understood that these embodiments are merely illustrative of various aspects of the invention. Thus, it is to be understood that numerous modification may be made in the illustrative embodiments and other arrangements may be devised without departing from the spirit and scope of the invention.

We claim:

1. A NSO myeloma cell transfected with a plasmid containing bcl-2 gene.

2. A NSO$^{bcl-2}$ myeloma cell line deposited with the American Type Culture Collection Rockville, Md. on Aug. 16, 1994 and catalogued as ATCC No. CRL 11705.

3. A hybridoma which is produced utilizing the NSO$^{bcl-2}$ myeloma cells deposited with the American Type Culture Collection, Rockville, Md. on Aug. 16, 1994 and catalogued as ATCC No. CRL 11705.

4. A method of producing a hybridoma comprising fusing B cells with NSO myeloma cells which are transfected with a plasmid containing bcl-2 gene.

5. The method of claim 4 wherein the plasmid is pCMVE.

6. The method of claim 4 wherein said plasmid contains an immunoglobulin heavy chain enhancer.

7. The method of claim 4 wherein the NSO myeloma cells are NSO$^{bcl-2}$ myeloma cells deposited with the American Type Culture Collection, Rockville, Md. on Aug. 16, 1994 and catalogued as ATCC No. CRL 11705.

8. Hybridoma produced by the method of claim 4.

9. A method of producing a monoclonal antibody comprising fusing B cells with NSO myeloma cells transfected with a plasmid containing bcl-2 gene so as to produce a monoclonal antibody-secreting hybridoma and obtaining a monoclonal antibody secreted by said hybridoma.

10. The method of claim 9 wherein the plasmid is pCMVE.

11. The method of claim 9 wherein said plasmid contains an immunoglobulin heavy chain enhancer.

12. The method of claim 9 wherein the NSO myeloma cells are NSO$^{bcl-2}$ myeloma cells deposited with the American Type Culture Collection, Rockville, Md. on Aug. 16, 1994 and catalogued as ATCC No. CRL 11705.

* * * * *